United States Patent [19]
Segev

[11] Patent Number: 5,908,845
[45] Date of Patent: Jun. 1, 1999

[54] POLYETHER NUCLEIC ACIDS

[76] Inventor: David Segev, 10 Hagoren, 76804 Mazkeret Batya, Israel

[21] Appl. No.: 08/740,516

[22] Filed: Oct. 30, 1996

[51] Int. Cl.$^6$ ...................... A61K 31/075; C07D 239/00; C07D 473/00

[52] U.S. Cl. ........................... 514/261; 514/44; 514/269; 514/885; 514/908; 536/25.3; 536/25.31; 536/25.32; 536/25.4; 536/43; 536/44; 536/23.1; 544/242; 544/264; 435/6

[58] Field of Search ............................. 514/44, 885, 908, 514/261, 269; 544/242, 264; 536/25.3, 25.31, 25.32, 23.1, 25.4, 43, 44; 435/6

[56] References Cited

U.S. PATENT DOCUMENTS

| | | | |
|---|---|---|---|
| 5,519,134 | 5/1996 | Acevedo et al. | 544/24.3 |
| 5,608,046 | 3/1997 | Cook et al. | 536/23.1 |
| 5,637,684 | 6/1997 | Cook et al. | 536/23.1 |
| 5,688,941 | 11/1997 | Cook et al. | 536/25.3 |
| 5,717,083 | 2/1998 | Cook et al. | 536/23.1 |

FOREIGN PATENT DOCUMENTS

| | | |
|---|---|---|
| WO86/05518 | 3/1986 | WIPO . |
| WO86/05519 | 3/1986 | WIPO . |
| WO89/12060 | 5/1989 | WIPO . |
| WO92/20702 | 5/1992 | WIPO . |

OTHER PUBLICATIONS

Burch et al, "Oligonucleotides Antisense to the Interlukin 1 Receptor mRNA Block the Effects of Interlukin 1 in Cultures Murine and Human Fibroblasts and in Mice", *J. Clin. Inv.*, vol. 88, pp. 1190–1196, (1991).

Calabretta et al, "Normal and leukemic hematopoietic cells manifest differential sensitivity to inhibitory effects of c–myb antisense ologideoxynucleotides: An in vitro study relevant to bone marrow purging", *Proc. Natl. Acad. Sci. USA*, vol. 88, pp. 2351–2355, (1991).

Dash et sl, "Selective elimination of mRNAs in vivo: Compementary ologideoxynucleotides promote RNA degradation by an Rnase H–like activity", *Proc. Natl. Acad. Sci. USA*, vol. 84, pp. 7896–7900, (1987).

Heikkila et al, "A c–myb antisense ologideoxynucleotide inhibits entry into S phase but not progress from $G_0$ to $G_1$", *Nature*, vol. 328, 445–449, (1987).

Nielson et al, "Sequence–Selective Recognition of DNA by Strand Displacement with a Thymine–Substituted Polyamide", *Science*, vol. 254, pp. 1497–1500, (1991).

Paterson et al, "Structural gene identification and mapping by DNA•mRNA hybrid–arrested cell–free translation", *Proc. Natl. Acad. Sci. USA*, vol. 74, No. 10, pp. 4370–4374, (1977).

Reed et al, "Antosense–mediated Inhibition of BCL2 Protooncogeene Expression and Leukemic Cell Growth and Survival: Comparisons of Phosphodester and Phosphorothioate Ologideoxynucleotides", *Cancer Research*, vol. 50, pp. 6565–6570, (1990).

Szczylik et al, "Selective Inhibition of Leukemia Cell Proliferation by BCR–ABL Antisense Ologideoxynucleotides", *Science*, vol. 253, pp. 562–565, (1991).

Uhlmann et al, "Antisense Ologideoxynucleotides: A New Therepeutic Principle", *Chem. Rev.*, vol. 90, No. 4, pp. 544–584, (1990).

Flam, F., "Can DNA Mimics Improve on the Real Thing?", *Science*, vol. 262, pp. 1647–1648, (1993).

Thuong et al, "Sequence–Specific Recognition and Modification of Double–helical DNA by Ologideoxynucleotides", *Angew. Chem. Int. Engl.*, vol. 32, pp. 666–690, (1993).

Zalipsky, S., "Functionalized Poly(ethylene glycol) for Preparation of Biologically Relevant Conjugates," *Bioconjugate Chem.*, vol. 6, pp. 150–165, (1995).

Cohen, J., "Ologideoxynucleotide therepeutics", *Trends in Biotechnology*, vol. 10, No. 3, pp. 87–91, (1992).

Delgado, C., "The Uses and Properties of PEG–Linked Proteins", *Critical Reviews in Therepeutic Drug Carrier Systems*, vol. 9, pp. 249–304, (1992).

Augustyns et al, "Influence of the incorporation of (S)–9–(3, 4–dihydroxybutyl) adenine on the enzymatic stability and base–pairing properties of ologideoxynucleotides", *Nucleic Acids Research*, vol. 19, No. 10, pp. 2587–2593, (1991).

Buchardt et al, "Peptide nucleic acids and their potential applications in biotechnology", *Tibtech*, vol. 11, pp. 384–386, (1993).

Agrawal, S., "Antisense ologideoxynucleotides as antiviral agents", *Tibtech*, vol. 10, No. 5, pp. 152–158, (1992).

Wahlestedt, C., "Antisense ologideoxynucleotide strategies in neuropharmacology", *TIPS*, vol. 15, pp. 42–46, (1994).

Cook, P.D., "Medicinal chemistry of antisense ologideoxynucleotides — future opportunities", *Anti–Cancer Drug design*, vol. 6, pp. 585–607, (1991).

Green, et al, "The Role of Antisense RNA in Gene regulation", *Ann. Rev. Biochem.*, vol. 55, pp. 569–597, (1986).

*Primary Examiner*—James O. Wilson
*Attorney, Agent, or Firm*—Mark M. Friedman

[57] ABSTRACT

A compound comprising a polyether backbone bearing a plurality of ligands that are individually bound to chiral carbon atoms located within said backbone, at least one of said ligands including a moiety selected from the group consisting of a naturally occurring nucleobase, a nucleobase binding group and a DNA intercalator; a process of synthesizing the compound, monomers to be used in this process and their synthesis process and processes for using the compound in biochemistry and medicine.

17 Claims, 4 Drawing Sheets

DNA

ENA

POLYETHER NUCLEIC ACIDS

FIELD AND BACKGROUND OF THE INVENTION

The present invention relates in general to nucleotide mimics and their derived nucleic acid mimics, methods for the construction of both and the use of the nucleic acid mimics in biochemistry and medicine. More particularly, the present invention relates to (i) acyclic nucleotide mimics, also referred to as acyclic nucleotides; (ii) a method for synthesizing the acyclic nucleotide mimics; (iii) acyclic nucleotide mimic sequences, also referred to as acyclic polynucleotide sequences; (iv) a method for synthesizing the acyclic nucleotide mimic sequences; and (v) use of the acyclic nucleotide mimic sequences as oligonucleotides in for example antisesnse procedures.

An antisense oligonucleotide (e.g., antisense oligodeoxyribonucleotide) may bind its target nucleic acid either by Watson-Crick base pairing or Hoogsteen and anti-Hoogsteen base pairing. To this effect see, Thuong and Helene (1993) Sequence specific recognition and modification of double helical DNA by oligonucleotides Angev. Chem. Int. Ed. Engl. 32:666. According to the Watson-Crick base pairing, heterocyclic bases of the antisense oligonucleotide form hydrogen bonds with the heterocyclic bases of target single-stranded nucleic acids (RNA or single-stranded DNA), whereas according to the Hoogsteen base pairing, the heterocyclic bases of the target nucleic acid are double-stranded DNA, wherein a third strand is accommodated in the major groove of the B-form DNA duplex by Hoogsteen and anti-Hoogsteen base pairing to form a triplex structure.

According to both the Watson-Crick and the Hoogsteen base pairing models, antisense oligonucleotides have the potential to regulate gene expression and to disrupt the essential functions of the nucleic acids. Therefore, antisense oligonucleotides have possible uses in modulating a wide range of diseases.

Since the development of effective methods for chemically synthesizing oligonucleotides, these molecules have been extensively used in biochemistry and biological research and have the potential use in medicine, since carefully devised oligonucleotides can be used to control gene expression by regulating levels of transcription, transcripts and/or translation.

Oligodeoxyribonucleotides as long as 100 base pairs (bp) are routinely synthesized by solid phase methods using commercially available, fully automated synthesis machines. The chemical synthesis of oligoribonucleotides, however, is far less routine. Oligoribonucleotides are also much less stable than oligodeoxyribonucleotides, a fact which has contributed to the more prevalent use of oligodeoxyribonucleotides in medical and biological research, directed at, for example, gene therapy or the regulation of transcription or translation levels.

Gene expression involves few distinct and well regulated steps. The first major step of gene expression involves transcription of a messenger RNA (mRNA) which is an RNA sequence complementary to the antisense (i.e., −) DNA strand, or, in other words, identical in sequence to the DNA sense (i.e., +) strand, composing the gene. In eukaryotes, transcription occurs in the cell nucleus.

The second major step of gene expression involves translation of a protein (e.g., enzymes, structural proteins, secreted proteins, gene expression factors, etc.) in which the mRNA interacts with ribosomal RNA complexes (ribosomes) and amino acid activated transfer RNAs (tRNAs) to direct the synthesis of the protein coded for by the mRNA sequence.

Initiation of transcription requires specific recognition of a promoter DNA sequence located upstream to the coding sequence of a gene by an RNA-synthesizing enzyme—RNA polymerase. This recognition is preceded by sequence-specific binding of one or more protein transcription factors to the promoter sequence. Additional proteins which bind at or close to the promoter sequence may upregulate transcription and are known as enhancers. Other proteins which bind to or close to the promoter, but whose binding prohibits action of RNA polymerase, are known as repressors.

There are also evidence that in some cases gene expression is downregulated by endogenous antisesnse RNA repressors that bind a complementary mRNA transcript and thereby prevent its translation into a functional protein. To this effect see Green et al. (1986) The role of antisense RNA in gene regulation. Ann. Rev. Biochem. 55:569.

Thus, gene expression is typically upregulated by transcription factors and enhancers and downregulated by repressors.

However, in many disease situation gene expression is impaired. In many cases, such as different types of cancer, for various reasons the expression of a specific endogenous or exogenous (e.g., of a pathogen such as a virus) gene is upregulated. Furthermore, in infectious diseases caused by pathogens such as parasites, bacteria or viruses, the disease progression depends on expression of the pathogen genes, this phenomenon may also be considered as far as the patient is concerned as upregulation of exogenous genes.

Most conventional drugs function by interaction with and modulation of one or more targeted endogenous or exogenous proteins, e.g., enzymes. Such drugs, however, typically are not specific for targeted proteins but interact with other proteins as well. Thus, a relatively large dose of drug must be used to effectively modulate a targeted protein.

Typical daily doses of drugs are from $10^{-5}$–$10^{-1}$ millimoles per kilogram of body weight or $10^{-3}$–10 millimoles for a 100 kilogram person. If this modulation instead could be effected by interaction with and inactivation of mRNA, a dramatic reduction in the necessary amount of drug could likely be achieved, along with a corresponding reduction in side effects. Further reductions could be effected if such interaction could be rendered site-specific. Given that a functioning gene continually produces mRNA, it would thus be even more advantageous if gene transcription could be arrested in its entirety.

Given these facts, it would be advantageous if gene expression could be arrested or downmodulated at the transcription level.

The ability of chemically synthesizing oligonucleotides and analogs thereof having a selected predetermined sequence offers means for dowmnodulating gene expression. Three types of gene expression modulation strategies may be considered.

At the transcription level, antisense or sense oligonucleotides or analogs that bind to the genomic DNA by strand displacement or the formation of a triple helix, may prevent transcription. To this effect see, Thuong and Helene (1993) Sequence specific recognition and modification of double helical DNA by oligonucleotides Angev. Chem. Int. Ed. Engl. 32:666.

At the transcript level, antisense oligonucleotides or analogs that bind target mRNA molecules lead to the enzymatic cleavage of the hybrid by intracellular RNase H. To this effect see Dash et al. (1987) Proc. Natl. Acad. Sci. U.S.A., 84:7896. In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing. To this effect see Chiang et al. (1991) Antisense oligonucleotides inhibit intercellular adhesion molecule 1 expression by two distinct mechanisms. J. Biol. Chem. 266:18162. As a result, in both cases, the number of the target mRNA intact transcripts ready for translation is reduced or eliminated.

At the translation level, antisense oligonucleotides or analogs that bind target mRNA molecules prevent, by steric hindrance, binding of essential translation factors (ribosomes), to the target mRNA, as described by Paterson et al. (1977) Proc. Natl. Acad. Sci. U.S.A., 74:4370, a phenomenon known in the art as hybridization arrest, disabling the translation of such mRNAs.

Thus, antisense sequences, which as described hereinabove may arrest the expression of any endogenous and/or exogenous gene depending on their specific sequence, attracted much attention by scientists and pharmacologists who were devoted at developing the antisense approach into a new pharmacological tool. To this effect see Cohen (1992) Oligonucleotide therapeutics. Trends in Biotechnology, 10:87.

For example, several antisense oligonucleotides have been shown to arrest hematopoietic cell proliferation (Szczylik et al (1991) Selective inhibition of leukemia cell proliferation by BCR-ABL antisense oligodeoxynucleotides. Science 253:562), growth (Calabretta et al. (1991) Normal and leukemic hematopoietic cell manifest differential sensitivity to inhibitory effects of c-myc antisense oligodeoxynucleotides: an in vitro study relevant to bone marrow purging. Proc. Natl. Acad. Sci. U.S.A. 88:2351), entry into the S phase of the cell cycle (Heikhila et al. (1987) A c-myc antisense oligodeoxynucleotide inhibits entry into S phase but not progress from G(0) to G(1). Nature, 328:445), reduced survival (Reed et al. (1990) Antisense mediated inhibition of BCL2 prooncogene expression and leukemic cell growth and survival: comparison of phosphodiester and phosphorothioate oligodeoxynucleotides. Cancer Res. 50:6565) and prevent receptor mediated responses (Burch and Mahan (1991) Oligodeoxynucleotides antisense to the interleukin I receptor m RNA block the effects of interleukin I in cultured murine and human fibroblasts and in mice. J. Clin. Invest. 88:1190). For use of antisense oligonucleotides as antiviral agents the reader is referred to Agrawal (1992) Antisense oligonucleotides as antiviral agents. TIBTECH 10:152.

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against intra- and extracellular nucleases; (iv) capability of penetration through the cell membrane; and (v) when used to treat an organism, low toxicity.

Unmodified oligonucleotides are impractical for use as antisense sequences since they have short in vivo half-lives, during which they are degraded rapidly by nucleases. Furthermore, they are difficult to prepare in more than milligram quantities. In addition, such oligonucleotides are poor cell membrane penetraters, see, Uhlmann et al. (1990) Chem. Rev. 90:544.

Thus it is apparent that in order to meet all the above listed requirements, oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done, nevertheless with little success.

Oligonucleotides can be modified either in the base, the sugar or the phosphate moiety. These modifications include the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester bridges, carbonate bridges, carboxymethyl ester bridges, acetamide bridges, carbamate bridges, thioether bridges, sulfoxy bridges, sulfono bridges, various "plastic" DNAs, x-anomeric bridges and borane derivatives. For further details the reader is referred to Cook (1991) Medicinal chemistry of antisense oligonucleotides—future opportunities. Anti-Cancer Drug Design 6:585.

International patent application WO 86/05518 broadly claims a polymeric composition effective to bind to a single-stranded polynucleotide containing a target sequence of bases. The composition is said to comprise non-homopolymeric, substantially stereoregular polymer molecules of the form:

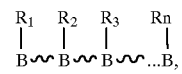

where:

(a) R1–Rn are recognition moieties selected from purine, purine-like, pyrimidine, and pyrimidine like heterocycles effective to bind by Watson/Crick pairing to corresponding, in-sequence bases in the target sequence;

(b) n is such that the total number of Watson/Crick hydrogen bonds formed between a polymer molecule and target sequence is at least about 15;

(c) B~B are backbone moieties joined predominantly by chemically stable, substantially uncharged, predominantly achiral linkages;

(d) the backbone moiety length ranges from 5 to 7 atoms if the backbone moieties have a cyclic structure, and ranges from 4 to 6 atoms if the backbone moieties have an acyclic structure; and (e) the backbone moieties support the recognition moieties at position which allow Watson-Crick base pairing between the recognition moieties and the corresponding, in-sequence bases of the target sequence.

According to WO 86/05518, the recognition moieties are various natural nucleobases and nucleobase-analogs and the backbone moieties are either cyclic backbone moieties comprising furan or morpholine rings or acyclic backbone moieties of the following forms:

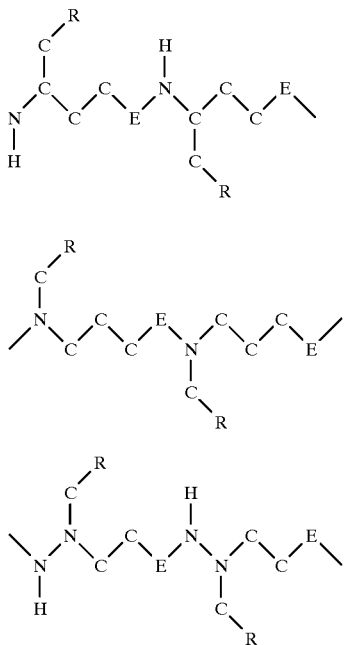

where E is —CO— or —SO$_2$—. The specification of the application provides general descriptions for the synthesis of subunits, for backbone coupling reactions, and for polymer assembly strategies. Although WO 86/05518 indicates that the claimed polymer compositions can bind target sequences and, as a result, have possible diagnostic and therapeutic applications, the application contains no data relating to the binding capabilities of a claimed polymer.

International patent application WO 86/05519 claims diagnostic reagents and systems that comprise polymers described in WO 86/05518, but attached to a solid support.

International patent application WO 89/12060 claims various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—SO$_2$—). However, the application provides no data supporting the specific binding of an oligonucleotide analog to a target oligonucleotide.

Nielsen et al. (1991) Science 254:1497, and International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other. To this effect of PNA heterohybrids see Biotechnology research news (1993) Can DNA mimics improve on the real thing? Science 262:1647.

PNA oligomers can be synthesized from the four protected monomers containing thymine, cytosine, adenine and guanine by Merrifield solid-phase peptide synthesis. In order to increase solubility in water and to prevent aggregation, a lysine amide group is placed at the C-terminal.

However, there are some major drawbacks associated with the PNA approach. One drawback is that, at least in test-tube cultures, PNA molecules do not penetrate through cell membranes, not even to the limited extent natural short DNA and RNA segments do. The second drawback is side effects which are encountered with toxicity. Because PNAs bind so strongly to target sequences, they lack the specificity of their natural counterparts and end up binding not just to target sequences but also to other strands of DNA, RNA or even proteins, incapacitating the cell in unforeseen ways.

There is thus a widely recognized need for, and it would be highly advantageous to have, oligonucleotide analogs devoid of these drawbacks which are characterized by (i) sufficient specificity in binding to target sequences; (ii) solubility in water; (iii) stability against intra- and extracellular nucleases; (iv) capability of penetrating through cell membranes; and (v) when used to treat an organism, low toxicity, properties that collectively render an oligonucleotide analog highly suitable as an antisense therapeutic drug.

SUMMARY OF THE INVENTION

According to the present invention there are provided nucleotide mimics and their derived nucleic acid mimics having a polyether backbone, methods for the construction of both and the use of the polyether nucleic acid mimics in biochemistry and medicine.

According to further features in preferred embodiments of the invention described below, provided is a compound comprising a polyether backbone (i.e., the backbone itself consisting only C—C and C—O bonds) bearing a plurality of ligands that are individually bound to chiral carbon atoms located within the backbone, at least one of the ligands including a moiety selected from the group consisting of a naturally occurring nucleobase (i.e., native nucleobase, e.g., A, C, G, T, U), a nucleobase binding group (i.e., a moiety which is not a native nucleobase, yet as native nucleobases may form hydrogen bonds with nucleobases in a fashion similar to native nucleobases, e.g., inosine, thiouracil, bromothymine, azaguanines, azaadenines, 5-methylcytosine) and a DNA intercalator. Thus the compound according to the invention may form specific interactions (e.g., hybridize) with native polynucleotides such as DNA and RNA.

According to still further features in the described preferred embodiments the chiral carbon atoms are separated from one another in the backbone by from four to six intervening atoms. Preferably five intervening atoms.

According to still further features in the described preferred embodiments the compound has the formula:

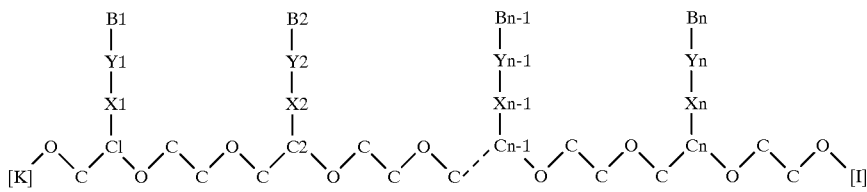

or the formula:

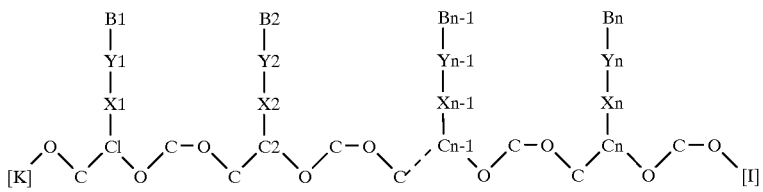

wherein, n is an integer greater than one, typically n is in the range of 5–20, preferably 7–15; each of B1–Bn is a chemical functionality group, at least one of the B1–Bn groups is a naturally occurring nucleobase, a nucleobase binding group or a DNA intercalator; each of Y1–Yn is a first linker group; each of X1–Xn is a second linker group; C1–Cn are chiral carbon atoms; and [K] and [R] are a first and second exoconjugates.

According to still further features in the described preferred embodiments each of the B1–Bn chemical functionality groups is independently selected from the group consisting of a hydrogen group, a hydroxy group, an amino group, an amido group, a sulfhydril group, a carboxylic group, a (C1–C3) alkanoyl group, an aromatic group, a heterocyclic group, a chelating agent and a reporter group.

According to still further features in the described preferred embodiments each of the Y1–Yn first linker groups is independently selected from the group consisting of an alkyl group, a phosphate group, a (C2–C4) alkylene chain, a (C2–C4) substitued alkylene chain and a single bond.

According to still further features in the described preferred embodiments each of the Y1–Yn first linker groups is independently selected from the group consisting of a methylene group and a C-alkanoyl group.

According to still further features in the described preferred embodiments each of the X1–Xn second linker groups is independently selected from the group consisting of a methylene group, an alkyl group, an amino group, an amido group, a sulfur atom, an oxygen atom, a selenium atom, a C-alkanoyl group, a phosphate derivative group, a carbonyl group and a single bond.

According to still further features in the described preferred embodiments m percents of the C1–Cn chiral carbons are in an S configuration, wherein m is selected from the group consisting of 90–95%, 96–98%, 99% and greater than 99%.

According to still further features in the described preferred embodiments [K] and/or [I] are each a polyethylene glycol moiety.

According to still further features in the described preferred embodiments the compound has the formula:

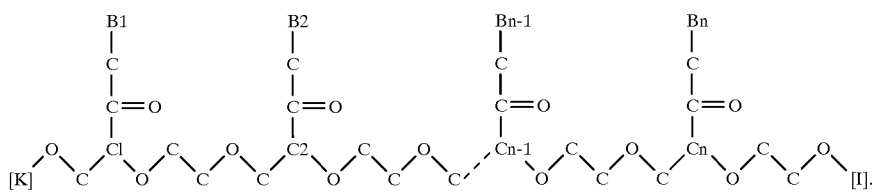

According to still further features in the described preferred embodiments the compound is interacted with ions of an alkaline, earth alkaline or transition metal.

According to still further features in the described preferred embodiments provided is a monomeric compound having a formula:

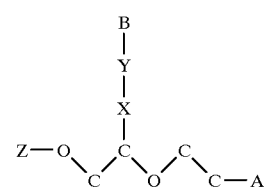

wherein, B is a chemical functionality group; Y is a first linker group; X is a second linker group; C is chiral carbon atoms; Z is a first protecting group; and A is a leaving group.

According to still further features in the described preferred embodiments the B chemical functionality group of the monomeric compound is a naturally occurring nucleobase or a nucleobase binding group, should the nucleobase include an amino group, the amino group is protected by a second protecting group.

According to still further features in the described preferred embodiments the Z protecting group is selected from the group consisting of a dimethoxytrityl group, a trityl group, a monomethoxytrityl group and a silyl group.

According to still further features in the described preferred embodiments the A leaving group is selected from the group consisting of a halide group, a sulfonate group, an ammonium derivative and a radical moiety that could be replaced by SN1 or SN2 mechanisms (for SN1 or SN2 mechanisms see Roberts and Caserio (1965) Basic principles of organic chemistry. U. A. Benjamin Inc. New-York, N.Y., page 292).

According to still further features in the described preferred embodiments the second protecting group is selected from the group consisting of a benzamido group, an isobutyramido group, a t-butoxycarbonyl group, a fluorenylmethyloxycarbonyl group and an acid labile group which is not cleaved by reagents that cleave the Z protecting group.

According to still further features in the described preferred embodiments the monomeric compound has the formula:

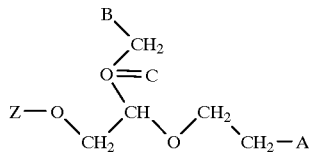

According to still further features in the described preferred embodiments provided is a process for preparing a compound according to the present invention, the process comprising the step of sequentially condensing monomers each having an ether moiety, the ether moiety including at least one ether linkage, the ether moiety further including at least one chiral carbon atom to which a functionality group being linked, at least one of the functionality groups is selected from the group consisting of a naturally occurring nucleobase, a nucleobase binding group and a DNA intercalator.

According to still further features in the described preferred embodiments provided is a process for preparing a compound according to the present invention, the process comprising the step of sequentially condensing a first monomers having an ether moiety, the ether moiety including at least one ether linkage, the ether moiety further including at least one chiral carbon atom to which a functionality group being linked, with at least one additional monomer, wherein at least one of the functionality groups is selected from the group consisting of a naturally occurring nucleobase, a nucleobase binding group and a DNA intercalator.

According to still further features in the described preferred embodiments provided is a process for sequence specific recognition of a double stranded polynucleotide, comprising the step of contacting the polynucleotide with a compound according to the present invention, such that the compound binds in a sequence specific manner to one strand of the polynucleotide, thereby displacing the other strand.

According to still further features in the described preferred embodiments provided is a process for sequence specific recognition of a single-stranded polynucleotide, comprising the step of contacting the polynucleotide with a compound according to the present invention, such that the compound binds in a sequence specific manner to the polynucleotide.

According to still further features in the described preferred embodiments provided is a process for modulating the expression of a gene in an organism comprising the step of administering to the organism a compound according to the present invention, such that the compound binds in a sequence specific manner DNA or RNA deriving from the gene.

According to still further features in the described preferred embodiments the modulation includes inhibiting transcription of the gene.

According to still further features in the described preferred embodiments the modulation includes inhibiting replication of the gene.

According to still further features in the described preferred embodiments the modulation includes inhibiting translation of the RNA of the gene.

According to still further features in the described preferred embodiments provided is a process for treating conditions associated with undesired protein production in an organism, comprising the step of contacting the organism with an effective amount of a compound according to the present invention, the compound specifically binds with DNA or RNA deriving from a gene controlling the protein production.

According to still further features in the described preferred embodiments provided is a process for inducing degradation of DNA or RNA in cells of an organism, comprising the steps of administering to the organism a compound according to the present invention, the compound specifically binds to the DNA or RNA.

According to still flirter features in the described preferred embodiments provided is a process for killing cells or viruses comprising the step of contacting the cells or viruses with a compound according to the present invention, the compound specifically binds to a portion of the genome or to RNA derived therefrom of the cells or viruses.

According to still further features in the described preferred embodiments provided is a pharmaceutical composition comprising a compound according to the present invention and at least one pharmaceutically effective carrier, binder, thickener, dilutent, buffer, preservative or surface active agent.

The present invention successfully addresses the shortcomings of the presently known configurations by providing an oligonucleotide analog characterized by (i) sufficient specificity in binding its target sequence; (ii) solubility in water; (iii) stability against intra- and extracellular nucleases; (iv) capability of penetrating through the cell membrane; and (v) when used to treat an organism, low toxicity, properties collectively rendering the oligonucleotide analog of the present invention highly suitable as an antisense therapeutic drug.

It is one object of the present invention to provide compounds that bind ssDNA and/or RNA strands to form stable hybrids therewith.

It is a further object of the invention to provide compounds that bind ssDNA and/or RNA strands more strongly then the corresponding DNA, yet less strongly then PNA.

It is another object to provide compounds wherein naturally-occuring nucleobases or other nucleobase-binding moieties are covalently bound to a polyether backbone.

It is yet another object to provide compounds other than RNA or PNA that can bind under in vivo conditions one strand of a double-stranded polynucleotide, thereby displacing the other strand.

It is yet a further object of the invention to provide a method for fabricating building blocks suitable for the fabrication of such compounds.

It is still a further object of the invention to provide a method for fabricating such compounds from their building blocks.

It is still another object to provide therapeutic and prophylactic methods that employ such compounds.

Additional objectives of the inventions are further described hereinbelow.

BRIEF DESCRIPTION OF THE DRAWINGS

The invention herein described, by way of example only, with reference to the accompanying drawings, wherein.

The file of this patent includes at least one drawing executed in color.

DESCRIPTION OF THE PREFERRED EMBODIMENTS

Figure 1A:
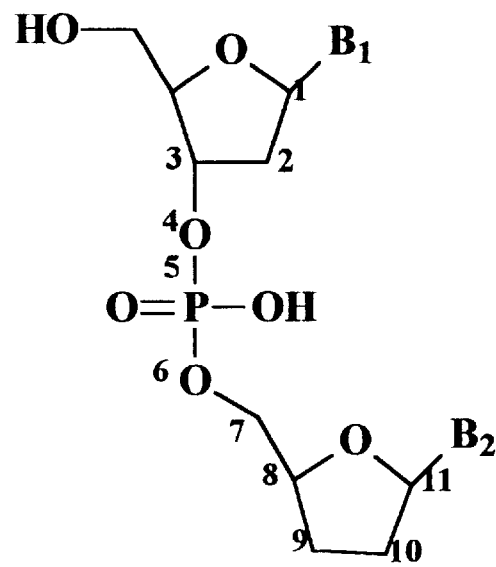
FIGS. 1a–b depicts the eleven atoms separating nucleobases on (a) prior art DNA and (b) and ENA compound according to the present invention.

The present invention is a compounds that are not polynucleotides yet which bind to complementary DNA and RNA sequences, the compounds according to the invention include naturally occurring necleobases or other nucleobases binding moieties (also referred herein as nucleobase analogs) covalently bound to a polyether backbone, which can be used as oligonucleotide analogs in for example antisense procedures. The oligonucleotide analogs according to the present invention include a new acyclic biopolymer backbone which best fulfills the five criteria for selecting antisense oligonucleotide analogs listed in the background section above.

The synthesis, structure and mode of operation of antisense oligonucleotide analogs according to the present invention may be better understood with reference to the drawings and accompanying descriptions.

The polyether poly(ethylene glycol) (PEG) is one of the best biocompatible polymers known, which possesses an array of useful properties. Among them, are a wide range of solubilities in both organic and aqueous media (Mutter et al. (1979) The Peptides Academic Press, 285), lack of toxicity and immunogenicity (Dreborg et al. (1990), Crit. Rev. Ther. Drug Carrier Syst. 6:315), nonbiodegradability, and ease of excretion from living organism (Yamaoka et al. (1994) J. Pharm. Sci. 83:601).

During the last two decades PEG was used extensively as a covalent modifier of a variety of substrates, producing conjugates which combine some of the properties of both the starting substrate and the polymer. See, Harris, J. M. (1992), Poly(ethylene Glycol) Chemistry, Plenum Press, New York.

The overwhelming majority of work in this area was prompted by a desire to alter one or more properties of a substrate of interest to make it suitable for a particular biological application. As the arsenal of PEG conjugates and their applications have increased it has become apparent that many undesirable effects triggered in vivo by various biological recognition mechanisms can be minimized by covalent modifications with PEG.

For example, using PEG conjugates, immunogenicity and antigenicity of proteins can be decreased. To this effect see U.S. Pat. No. 4,179,337 to Davis et al. Thrombogenicity as well as cell and protein adherence can be reduced in the case of PEG-grafted surfaces. To this effect see Merrill (1992) Poly(ethylene Glycol) Chemistry, page 199, Plenum Press, New York. These beneficial properties conveyed by PEG are of enormous importance for any system requiring blood contact. For further information concerning the biocompatibility of PEG, the reader is referred to Zalipski (1995) Functionalized poly(ethylene glycol) for preparation of biologically relevant conjugates. Bioconjugate Chem 6:150. However, all so far known PEG conjugates are exoconjugates, wherein the conjugated moiety is conjugated at one of the terminal hydroxyl groups of PEG (see formula I below).

Due to its biocompatible properties, PEG is use, according to preferred embodiment of the present invention, as a backbone to which nucleobases, nucleobase analogs (i.e., nucleobase binding moieties) and/or other chemical groups that interact with nucleic acids (e.g., DNA intercalators) are covalently linked to form oligonuleotide analogs having desired characteristics, as is further detailed below.

Thus, in the broad sense, the present invention provides a new class of acyclic backbone DNA compounds, that complementary bind single-stranded (ss) DNA and RNA strands. These compounds are herein referred to as polyether nucleic acids (ENAs). The compounds of the invention generally include (i) a polyether backbone (i.e., a backbone consisting of only C—C and C—O bonds) and (ii) chemical functionality groups at least some of which are capable of forming suitable hydrogen bonds in a complementary manner with ssDNA and RNA. Representatives chemical functionality groups include either the five naturally occurring DNA and RNA nucleobases, i.e., thymine, adenine, cytosine, uracil or guanine, or modified bases such as but not limited to inosine, thiouracil, bromothymine, azaguanines, azaadenines, 5-methylcytosine, typically attached to a polyether backbone such as PEG via a suitable linker arm made of one or more linker groups, such that, in a preferred embodiment of the invention, adjacent chemical functionality groups are separated form one another by eleven atoms, mimicking native DNA.

PEG is of a formula $HO-(CH_2CH_2O)_n-CH_2CH_2OH$, repeated in (I):

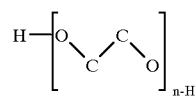

In one embodiment of the invention, the polyether nucleic acid compound has the general formula (II):

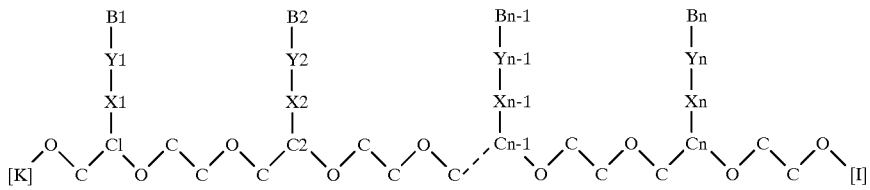

wherein, each of B1–Bn is a chemical functionality group each of Y1–Yn is a first linker group; each of X1–Xn is a second liker group; C1–Cn are chiral carbon atoms; and [K] and [I] area first and second exoconjugates.

According to a preferred embodiment of the invention, the chemical funtionality groups B1–Bn are naturally occurring or analog necleobases attached to the backbone in a predetermined selected order, forming a sequence Preferably the nucleobases are attached to Y via the position found in nature, i.e., position 9 for purines (e.g., adenine and guanine), and position 1 for pyrimidines (e.g., uracyl, thymine and cytosine).

In addition, for various purposes, some of the chemical functionality groups B1–Bn may be a hydroxy group, an amino group, an amido group, a sulfhydril group, a carboxylic group, a (C1–C3) alkanoyl group, an aromatic group, a heterocyclic group, a chelating agent (e.g., EDTA, EGTA, a diol group such as a vicinal diol group, a triol group and the like).

In order to improve binding both to double-stranded and single-stranded DNA, some B1–Bn functionality groups may be a DNA intercalator such as but not limited to an antraquinone group and the like.

Furthermore, one or more of the functionality groups B1–Bn may include a reporter molecule such as, for example, a fluorophor, a radioactive label, a chemluminescent agent, an enzyme, a substrate, a receptor, a ligand, a hapten, an antibody and the like, such that the compound may serve as a labeled or detectable probe in hybridization assays.

Yet furthermore, any one or more of the B1–Bn chemical functionality groups can be a ligand capable of interacting and covalently alter a complementary DNA or RNA strand. Suitable ligands include natural or analog nucleobase modified with an alkylating electrophile, such as but not limited to 3-(iodoacetamido)propyl, in position 5 of deoxyuridine. In the later case, the modified compound, may upon base pairing with a complementary target nucleic acid strand, to covalently cross link with the 7-position of a guanine residue present in the complementary DNA or RNA strands. Subsequently depurination of the cross-linked guanine and strand scission of the complementary strand may naturally occur under in vivo conditions. To this effect the reader is referred to Meyer et al. (1989) Efficient specific cross-linking and cleavage of DNA by stable synthetic complementary oligodeoxynucleotides. J. Am. Chem. Soc. 111:8517.

Each of Y1–Yn first linker groups can be an alkyl group such as a secondary carbon atom, a tertiary carbon atom or a phosphate group. Preferably, each of the Y1–Yn linker groups is a methylene group or a C-alkanoyl group. Furthermore, each of the Y1–Yn linker groups can be a (C2–C4) alkylene chain or a (C2–C4) alkylene chain substituted with $R_1R_{22}$. In some cases Y can be just a single bond.

Each of the X1–Xn second linker groups can be a methylene group (or carbon atom substituted with alkyl groups as $R_1R_2$), an amino group, an amido group, a sulfur atom, an oxygen atom, a selenium atom, a C-alkanoyl group, a phosphate derivative group (e.g. methyl phosphate and phosphoamidate), or preferably a carbonyl group. In some cases X can be just a single bond.

Figure 1B:
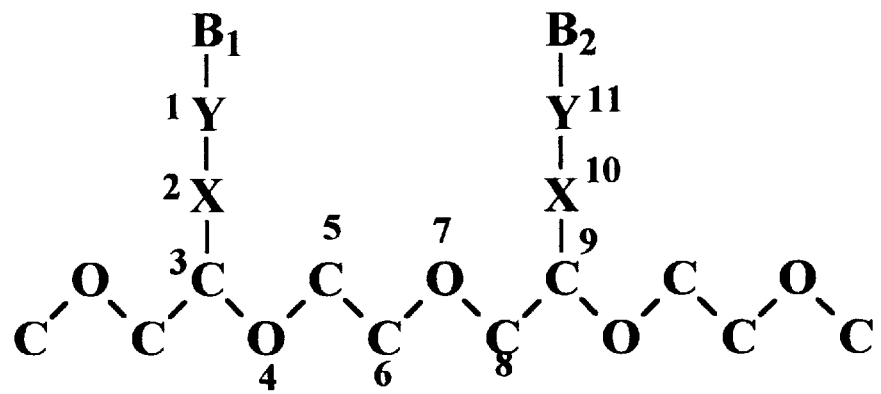

With reference now to FIGS. 1a–b, in accordance with the teachings of the present invention, the X and Y groups serve as linker arms to ensure the presence of preferably eleven atoms spacing between adjacent chemical functionality groups B, as is the case in natural nucleic acids. FIGS. 1a–b present two adjacent nucleobases (B) on a DNA strand (FIG. 1a) and on an ENA strand according to the preferred embodiment of the invention (FIG. 1b).

C1–Cn are chiral carbon atoms. The chirality of these atoms may be selected either of S or R configurations. Presently, the S configuration is preferred. As is further detailed hereinbelow, the compound according to the invention is built in a stepwise manner, wherein each monomer or building block is sequentially added to a growing polymer. Therefore, provided that the building blocks can be prepared with a desired chirality (i.e., R or S configurations) a compound of predetermined yet mixed S and R configurations C1–Cn chiral carbons can be prepared.

Further according to the invention, [K] and [I] are a first and second exoconjugates such as but not limited to a polyethylene glycol (PEG) moieties each having one or more repeat units or a hydrogen atom. Exoconjugate [K] and [I] may be water soluble or water insoluble polymers. Such conjugates can be used to modulate the ability of the compound to cross cell membranes. Nevertheless, any one or both [K] and [I] may be a hydrogen atom.

A preferred polyether nucleic acid molecule according to the invention have the general formula (III):

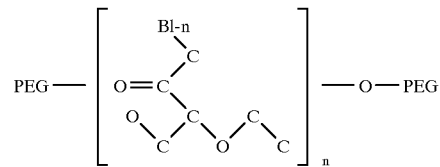

wherein, each of B1–Bn is a chemical functionality group such as a natural nucleobase or a nucleobase analog and PEG is polyethylene glycol.

Presently, the most preferred embodiment is the compound having the above general formula III, wherein B is a natural nucleobase, i.e., thymine (T), adenine (A), cytosine (C), guanine (G) and uracil (U), and wherein n is an integer in the range of 4 to 50, preferably in the range of 8 to 30, most preferably in the range of 12–22.

Figure 2:
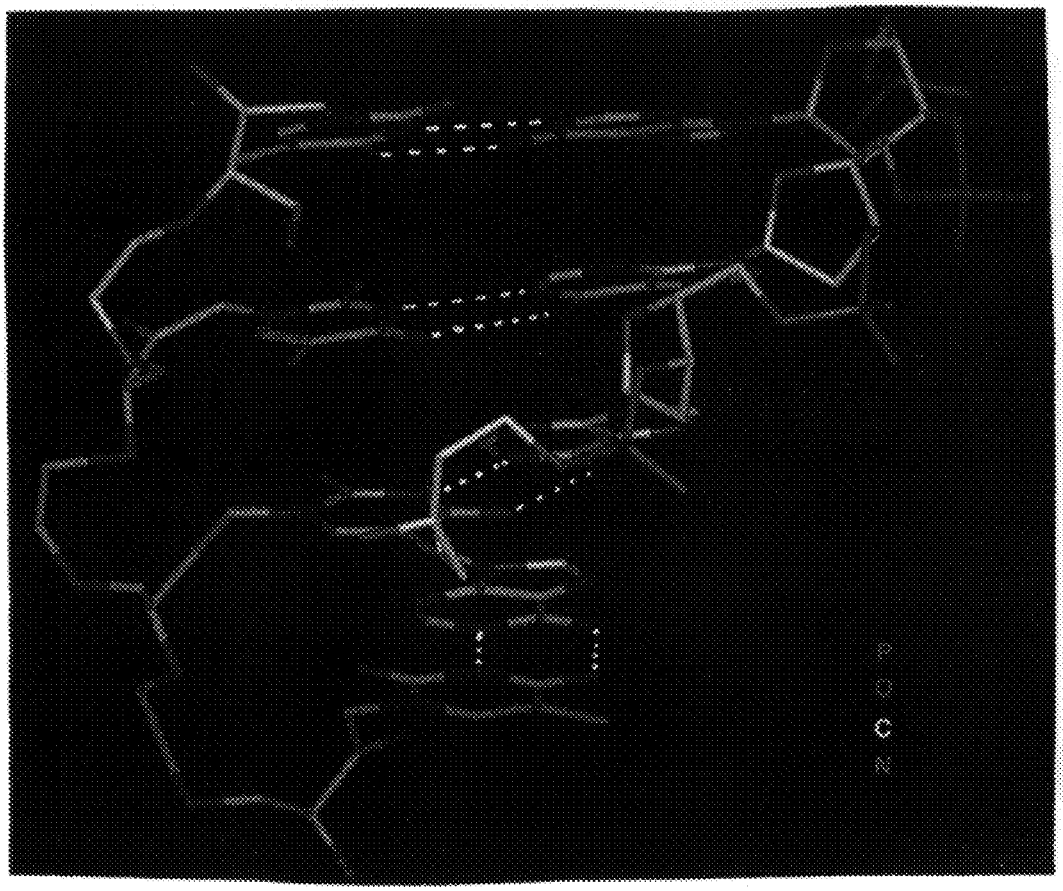
FIG. 2 is a molecular model presenting hybridization of a tetra-thymine-ENA compound having eleven atoms between adjacent B functionality groups according to the present invention with natural tetra-adenine-ssDNA.

With reference now to FIG. 2, molecular modeling that represents the hybridization of a tetra-thymidine-ENA compound according to formula III above with natural adenine tetra nucleotide predicts a perfect hybridization match of the hydrogen bonds of the hybrid with minimum energy, wherein O is presented in red; C in yellow; N in blue, P in purple and the hydrogen bonds formed are emphasized by dashed lines, connecting the relevant atoms.

The polyether nucleic acids of the present invention may be synthesized using standard DNA synthesis procedures, either in solution or on a solid phase.

The building blocks used are specially designed chiral (S) monomer triols or their activated forms.

The monomer building blocks according to the invention are preferably triols or ketotriols having the general formula (IV):

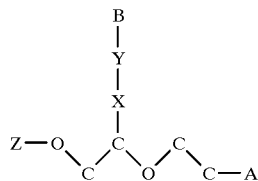

wherein B, Y and X are as defined above; Z is a suitable protecting group; and A is a suitable leaving group.

Should a specific building block include B which is a natural or analog nucleobase, the amino groups thereof may be protected with any conventional protecting group, such as but not limited to a benzamido group, an isobutyramido group, a t-butoxycarbonyl (Boc) group, a fluorenylmethyloxycarbonyl (Fmoc) group and the like.

Z is a protecting group for protecting the terminal hydroxyl group of the monomer. Z can be any suitable protecting group known in the art, such as but not limited to a dimethoxytrityl group, a trityl group, a monomethoxytrityl group or a silyl group. Preferably Z is a dimethoxytrityl group.

A is a leaving group such as a halide group, a sulfonate group, an ammonium derivative, or any radical moiety that could be replaced by SN1 or SN2 mechanisms.

A preferred monomer building block according to the invention have the general formula (V):

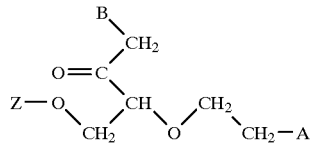

wherein, B, Z and A are as defined above.

According to another embodiment of the present invention, the polyether nucleic acid compound has the general formula (VI):

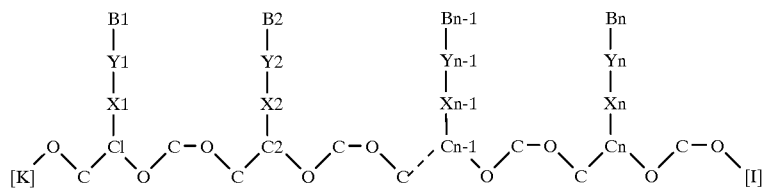

wherein B1–Bn, Y1–Yn, X1–Xn, [K] and [I] are all as described above in detail. The difference between the compounds generally described by formula VI and the compounds generally described by formula II is in the number of atoms present between adjacent B functionality groups. While in the compound described by formula II present are eleven such atoms, in the compound described by formula VI present are only ten atoms, as the carbon at position 6 (or 5) as shown in FIG. 1b is removed to yield an C—O—C bond.

Figure 3:
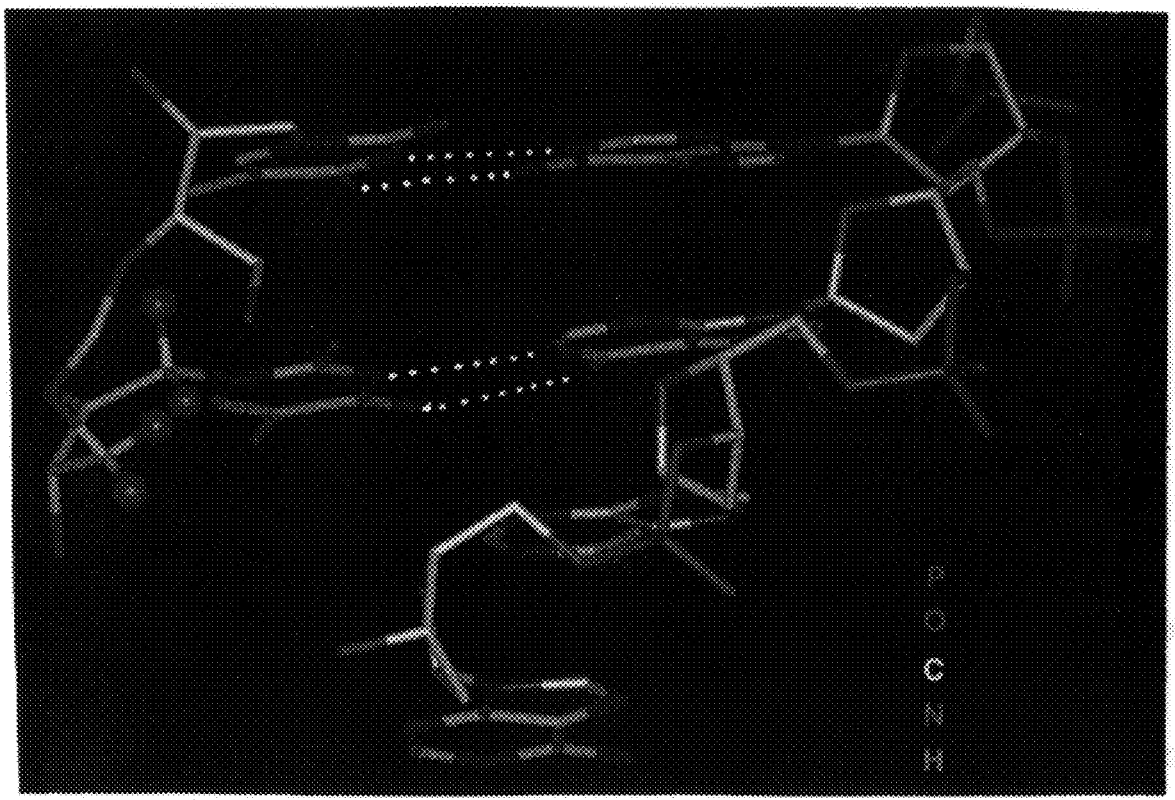
FIG. 3 is a molecular model presenting hybridization of a dithymidine-ENA compound having ten atoms between adjacent B functionality groups according to the present invention with natural triadenine-ssDNA.

With reference now to FIG. 3, computer modeling of a compound following general formula VI, made of two monomers, wherein X1 and X2 are carbonyl groups, Y1 and Y2 are —CH$_2$— groups and B1 and B2 are thymine nucleobases, paired with two adenine residues of an adenine trinucleotide, reveals that a steric conformational constrain is imposed by certain hydrogen atoms (highlighted in green) of the —CH$_2$— linker group and a —CH$_2$— group on the polyether backbone, such that pairing is energetically unfavorable and therefore not likely to occur.

Figure 4:
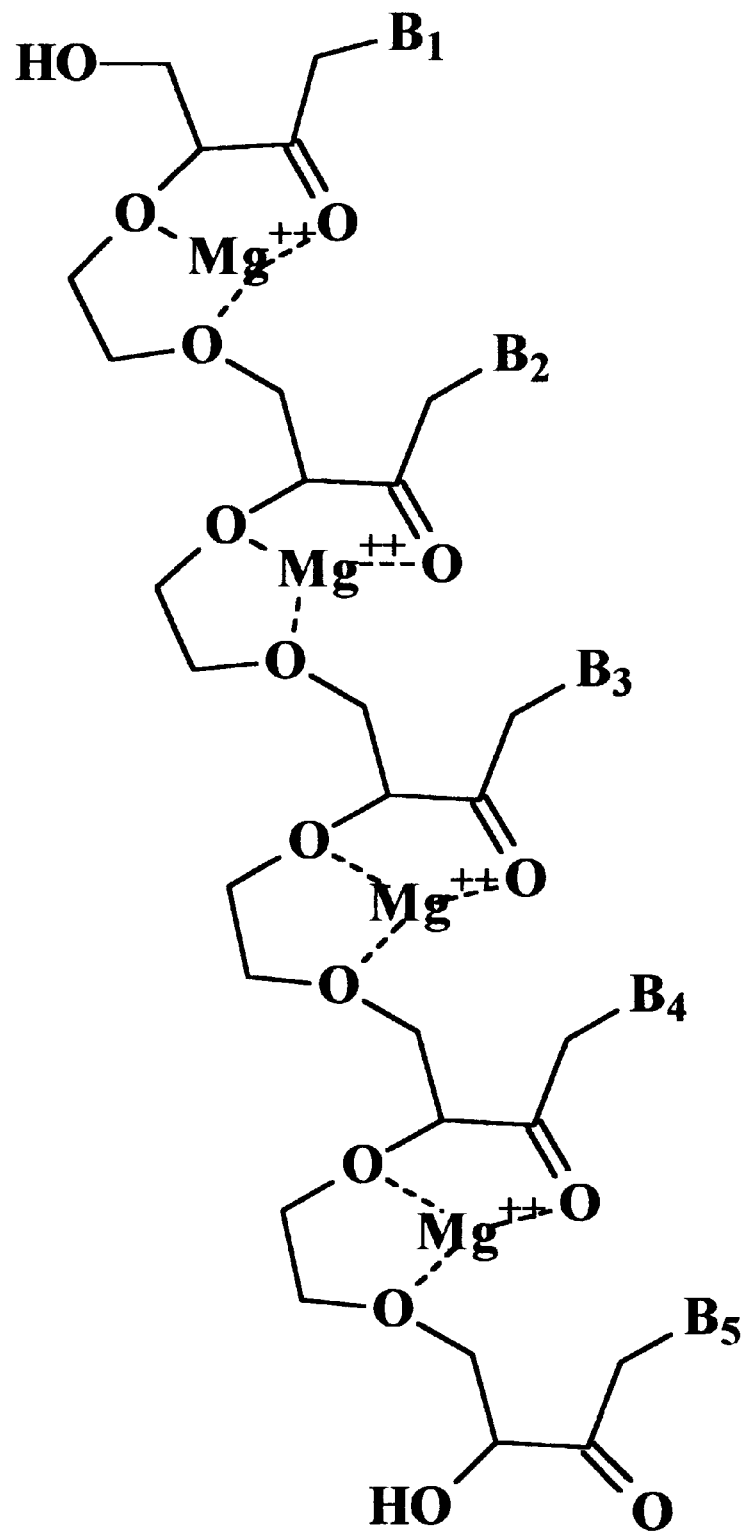
FIG. 4 presents possible coordinative interaction of ENA according to the invention with $Mg^{++}$ ions, which interactions may facilitate pairing with complementary sequences.

With reference now to FIG. 4, in a preferred embodiment of the invention a polyether nucleic acid according to any of the embodiments described hereinabove is interacted with ions of an alkaline metal such as but not limited to Na$^+$, earth alkaline metal such as but not limited to Ca$^{++}$ and Mg$^{++}$, or ions of a transition metal such as but not limited to Fe$^{++}$, Zn$^{++}$, Cu$^{++}$, Mn$^{++}$ and Cr$^{++}$, capable of forming coordinative or other bonds with oxygen atoms or other electronegative moieties of the polyether backbone and/or the linker groups. Such coordinative bonds may assist in bringing the polyether nucleic acids according to the invention to a conformation highly suitable for base pairing with a complementary single-stranded DNA or RNA. In the example of FIG. 4, Mg$^{++}$ ions are shown each to form three coordinative bonds with a polyether nucleic acid, two of which are with two adjacent oxygen atoms of the polyether backbone and one additional bond is formed with an oxygen atom of a carbonyl linker group.

The present invention is further directed at use of ENA molecules in solid-phase biochemistry (see, Solid-Phase Biochemistry—Analytical and Synthetic Aspects (1983) W. H. Scouten, ed., John Wiley & Sons, New York), notably solid-phase biosystems, especially bioassays or solid-phase techniques which concerns diagnostic detection/quantitation or affinity purification of complementary nucleic acids (see, Affinity Chromatography—A Practical Approach (1986) P. D. G. Dean, W. S. Johnson and F. A. Middle, IRL Press Ltd., Oxford; Nucleic Acid Hybridization—A Practical Approach (1987) B. D. Harnes and S. J. Higgins, IRL Press Ltd., Oxford).

Present day methods for performing such bioassays or purification techniques almost exclusively utilize "normal" or slightly modified oligonucleotides either physically absorbed or bound through a substantially permanent covalent anchoring linkage to solid supports such as cellulose, glass beads, including those with controlled porosity (mizutani, et al, (1986) J. Chromatogr. 356:202), "Sepharose", "Sephadex", polyacrylamide, agarose, hydroxyalkyl methacrylate gels, porous particulate alumina, porous ceramics, diobonded silica, or contiguous materials such as filter discs of nylon or nitrocellulose. One example employs the chemical synthesis of oligo-dT on cellulose beads for the affinity isolation of poly A tail containing mRNA (Gilham in Methods in Enzymology (1971) L. Grossmann and K. Moldave, eds., vol. 21, part D, page 191, Academic Press, New York and London).

All the above-mentioned methods are applicable within the context of the present invention. However, when possible, covalent linkage is preferred over the physical adsorption of the molecules in question, since the latter approach has the disadvantage that some of the immobilized molecules can be washed out (desorbed) during the hybridization or affinity process.

There is, thus, little control of the extent to which a species adsorbed on the surface of the support material is lost during the various treatments to which the support is subjected in the course of the bioassay/purification procedure. The severity of this problem will, of course, depend to a large extent on the rate at which equilibrium between adsorbed and "free" species is established. In certain cases it may be virtually impossible to perform a quantitative assay with acceptable accuracy and/or reproducibility. Loss of adsorbed species during treatment of the support with body fluids, aqueous reagents or washing media will, in general, be expected to be most pronounced for species of relatively low molecular weight.

Thus, ENA species benefit from the above-described solid-phase techniques with respect to the much higher (and still sequence-specific) binding affinity for complementary nucleic acids and from the additional unique sequence-specific recognition of (and strong binding to) nucleic acids present in double-stranded structures. They can therefore replace common oligonucleotides in hybridization assays such as but not limited to blot hybridizations ("Southern" and "Northern"), dot blot hydridizations, reverse blot hybridizations, in situ hybridizations, liquid phase hybridizations, clones (bacteria/phages, etc.) screening and in other assays involving hybridizations such as but not limited to PCR, sequencing, primer extension and the like.

They also can be loaded onto solid supports in large amounts, thus further increasing the sensitivity/capacity of the solid-phase technique. Further, certain types of studies concerning the use of ENA in solid-phase biochemistry can be approached, facilitated, or greatly accelerated by use of the recently-reported "light-directed, spatially addressable, parallel chemical synthesis" technology (Fodor, et al. (1991) Science, 251:767), a technique that combines solid-phase chemistry and photolithography to produce thousands of highly diverse, but identifiable, permanently immobilized compounds (such as proteins) in a substantially simultaneous way.

The present invention is further directed at therapeutic and/or prophylactic uses for polyether nucleic acids (ENAs). Likely therapeutic and prophylactic targets according to the invention include but are not limited to human papillomavirus (HPV), herpes simplex virus (HSV), candidia albicans, influenza virus, human immunodeficiency virus (HIV), intracellular adhesion molecules (ICAM), cytomegalovirus (CMV), phospholipase A2 (PLA2), 5-lipoxygenase (5-LO), protein kinase C (PKC), and RAS oncogene.

Potential applications of such targeting include but are not limited to treatments for labial, ocular and cervical cancer; genital warts; Kaposi's sarcoma; common warts; skin and systemic fungal infections; AIDS; pneumonia; flu; mononucleosis; retinitis and pneumonitis in immunosuppressed patients; ocular, skin and systemic inflammation; cancer; cardiovascular disease; psoriasis; asthma; cardiac infarction; cardiovascular collapse; kidney disease; gastrointestinal disease; osteoarthritis; rheumatoid arthritis; septic shock; acute pancreatitis; and Crohn's disease.

For therapeutic or prophylactic treatment, the polyether nucleic acids of the present invention can be formulated in a pharmaceutical composition, which may include thickeners, carriers, buffers, diluents, surface active agents, preservatives, and the like, all as well known in the art. Pharmaceutical compositions may also include one or more active ingredients such as but not limited to antiinflammatory agents, antimicrobial agents, anesthetics and the like in addition to polyether nucleic acids.

The pharmaceutical composition may be administered in either one or more of ways depending on whether local or systemic treatment is of choice, and on the area to be treated. Administration may be done topically (including ophtalmically, vaginally, rectally, intranasally), orally, by inhalation, or parenterally, for example by intravenous drip or intraperitoneal, subcutaneous, or intramuscular injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons ordinarily skilled in the art can easily determine optimum dosages, dosing methodologies and repetition rates.

Treatments of this type can be practiced on a variety of organisms ranging from unicellular prokaryotic and eukaryotic organisms to multicellular eukaryotic organisms. Any organism that utilizes transcription (including DNA-RNA transcription and reverse transcription), RNA transcripts or RNA-protein translation as a fundamental part of its hereditary, metabolic or cellular control is susceptible to therapeutic and/or prophylactic treatment in accordance with the present invention. Seemingly diverse organisms such as yeast, bacteria, algae, protozoa, all plants and all higher animal forms, including warm-blooded animals, can be treated.

Further, each cell of multicellular eukaryotes can be treated since they include both DNA-RNA transcription and RNA-protein translation as integral parts of their cellular activity.

Furthermore, many of the organelles (e.g., mitochondria, chloroplasts and chromoplasts) of eukaryotic cells also include transcription and translation mechanisms. Thus, single cells, cellular populations or organelles can also be included within the definition of organisms that can be treated with therapeutic or diagnostic phosphorothioate oligonucleotides. As used herein, therapeutics is meant to include the eradication of a disease state, by killing an organism or by control of erratic or harmful cellular growth or expression.

Polyether nucleic acids (ENAs) according to the present invention enjoy various advantages over existing oligonucleotide analog technologies.

First, according to a preferred embodiment of the invention, the ENAs' backbone is PEG, known to be soluble both in aqueous and in organic solvents, in high concentrations. The polyether backbone of ENAs according to the invention possess hydrophobicity on one hand and solubility in water on the other. This unique characteristic of ENAs enables a balanced hybridization between ENAs and complementary DNA or RNA molecules, as ENAs do not interact too strong with complementary sequences as protein nucleic acids (PNAs) do, yet ENAs are not highly solvated in aqueous media as native DNA and RNA strands.

Second, one of the major drawbacks of PNAs when used as antisense molecules is that PNA-DNA hybrids are characterized by high melting temperature (Tm). For example, the Tm value for a duplex such as PNA-$T_{10}$-$dA_{10}$ is greater than 70° C., whereas the Tm value of the equivalent native double stranded DNA ($dT_{10}$-$dA_{10}$) is nearly three fold lower, about 24° C. Because PNAs bind complementary sequences so strongly, at body temperature (e.g., 37° C.) PNAs lack the specificity to their intended counterparts and end up binding not just to target sequences but also to other strands of DNA, RNA, or even proteins, incapacitating the cell in unforeseen ways. PNAs act as a micelle when the lysine residues are solvated. PNAs are poorly miscible in water, while the hydrophobic nature of the backbone have a tendency to seek for a nonpolar environment e.g., the bases of the natural complementary DNA. These hydrophobic interactions are the major driving force for the formation of highly stable PNA-DNA hybrid and therefore very high Tm values for such hybrids. The unique solubility nature of ENAs, by conserving the hydrophobic-hydrophilic properties of polyethers such as PEG, yield Tm values slightly higher than natural DNA, yet much lower values than PNAs, which moderate values are of great importance for specificity.

Third, polyether compounds such as cyclodextrins have a tendency to form helices, which are stabilized in solution by water and metal ions under physiological conditions. This phenomenon is schematically illustrated for an ENA compound according to the invention in FIG. 4. This characteristic of polyether compounds renders these compounds highly suitable acyclic backbones for nucleobases to be base paired with complementary DNA or RNA molecules.

Fourth, PEG is approved by the FDA for parenteral use, topical application, and as a constituent of suppositories, nasal sprays, foods and cosmetics. PEG is of low toxicity when administered orally or parenterally, and only large quantifies involve adverse reactions. See, Smyth, H. F. et al. (1955) J. Am. Pharm. Assoc., 34:27. Evidences accumulated experiencing administration of PEG-protein conjugates, suggest that both the plasma half-lives (circulating time) of PEG conjugated proteins and their bioavailability improves as compared with the native proteins, which improvement is accompanied by improved efficacy. Ganser et al. (1989) Blood, 73:31, observed less side effects at lower dosage using PEG-modifications. Reduced toxicity has been observed with several PEG-modified enzymes, see Fuertges et al. (1990) J. Contr. Release, 11:139. Another advantage in exploiting the improved pharmacokinetics of PEG is the option of administrating bolus injections instead of continuous intravenous infusions, as described by Pizzo (1991) Adv. Drug Del. Rev. 6:153. In the preferred embodiments of the invention, ENAs include a PEG backbone and/or are conjugated to PEG exoconjugates and therefore enjoy the above listed advantages.

Finally, as is further detailed in the Examples section below, ENAs synthesis preferably involves using monomers having one chiral center with known chirality. This monomer (formula V) is condensed as much as needed to prepare the appropriate oligonucleotide having a polyether backbone and a preselected and desirable nucleobases sequence. During these condensations, the chiral center is not susceptible to racemization. As is further detailed in the Examples section hereinbelow, the synthesis of the monomers involves a chiral starting material which is available in a desired chirality in a pure form. In contrast, Miller et al. (1971) J. Am. Chem. Soc. 93:6657, has prepared non-ionic oligonucleotide analogs, in which the hydroxyl group in the phosphate moiety is replaced by a methyl group to yield methylphosphonate linkages. As shown by Miller, each methylphosphonate linkage (p) may have an R or an S chiral configuration. Thus for example, dApA(S)(dA)$_{12}$ hybridized to poly dT has a Tm value higher by 4.4° C. as compared with dApA(R)(dA)$_{12}$. This observation suggests that the methyl groups in the R configuration may provide some specific steric hindrance. Since there is an equal chance per each synthesis step for R or S configurations, which decreases dramatically the Tm, introduction of more than four methylphosphonates in an oligonucleotide chain typically results in Ca. 20° C. decrease in Tm values. Obviously, it is impossible to separate between the diastereoisomers formed in each step of synthesis. The same argumentation is for the replacement of hydroxyl groups with sulfhydril groups in the phosphate moiety as in phosphothioate oligonucleotide analogs. Furthermore, these materials are sparingly soluble in water. The solubility of this family of compounds in aqueous buffers depends on the size, composition and possibly even the sequence of the oligomer. A high percentage of guanine, or even worse, an aggregate of contiguous guanine residues, sharply reduces the solubility of such compounds. For example, d(CpT)$_8$ is soluble up to millimolar concentrations, whereas a d(ApG)$_8$ has solubility of less than 0.1 mM.

Additional objects, advantages, and novel features of ENAs will become apparent to one ordinarily skilled in the art upon examination of the following examples, which are not intended to be limiting.

EXAMPLE 1

Preparation of a Monomer Described by Formula V

Chirality selection

The starting material for synthesizing a monomer according to formula V above is preferably (S)-(+)-Erythrulose hydrate (Aldrich). This compound has a chiral center which possesses the appropriate S configuration. Protection of the vicinal diols as acetonide is performed by dissolving 13.8 grams of (S)-(+)-Erytrulose hydrate in 11 ml acetic acid. The solvent is then removed by co-evaporation with 22 ml of added toluene. The obtained residue is dissolved in 10% of 1,2-dimethoxypropane in 30 ml acetone containing a catalytic amount (1.9 grams) of p-toluenesulfonic acid. The mixture is stirred at room temperature for 30 minutes. 1.6 grams of sodium acetate are then added, the mixture is filtered and the obtained residue is chromatographed on a silica gel using ethylacetate/hexane (3/7) as the chromatographic carrier to afford Ca. 8.0 grams (50%) of 3,4-O-isopropylidene-(+)-erythrulose (compound A) as an oil.

This process is briefly described by equation 1:

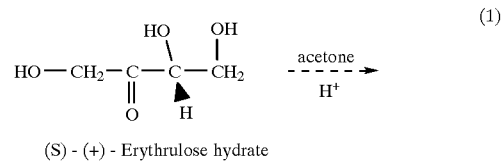

(S) - (+) - Erythrulose hydrate

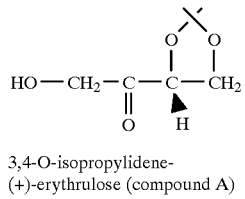

3,4-O-isopropylidene-
(+)-erythrulose (compound A)

Protection of the carbonyl group

The carbonyl group of the 3,4-O-isopropylidene-(+)-erythrulose (compound A) may be protected as dithian by reacting 3,4-O-isopropylidene-(+)-erythrulose with excess of methyl-trimethylsilylthiol (The later reagent is prepared according to Evans et al. (1977) J. Am. Chem. Soc. 99:5009), and ZnI$_2$ in ether. The reaction is monitored on a TLC plate. At the end of the reaction, concentrated ammonia is added, and the resulting product is extracted with ether. The dithian compound thus obtained (compound B) is preferably purified by silica gel column chromatography using ethylacetate/hexane (3/7) as the eluent.

This process is briefly described by equation 2:

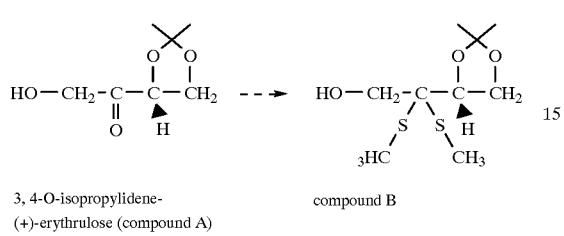

Preparation of (S)-4-O-methanesulfonyl-1,2-3-dithian butanetriol

The product of Equation 2 (compound B), is co-evaporated with pyridine, and thereafter dissolved in same. The obtained solution is cooled to 0° C. using an ice-water bath, 1.5 mole equivalents of methanesulfonyl-chloride are added dropwise and the mixture is thereafter stirred for two hours at room temperature. The reaction mixture is then re-cooled to 0° C., 20 ml of methanol are added and the solvent is evaporated. The residual oil thus obtained is dissolved in 300 ml ethylacetate, washed twice with 300 ml of saturated NaHCO$_3$ solution and the aqueous layers extracted three times with 300 ml ethylacetate. The combined organic layers are dried over anhydrous sodium sulfate, evaporated and purified by column chromatography on silica gel as described above to obtain (S)-4-O-methanesulfonyl-1,2-3-dithian butanetriol (compound C).

This process is briefly described by equation 3:

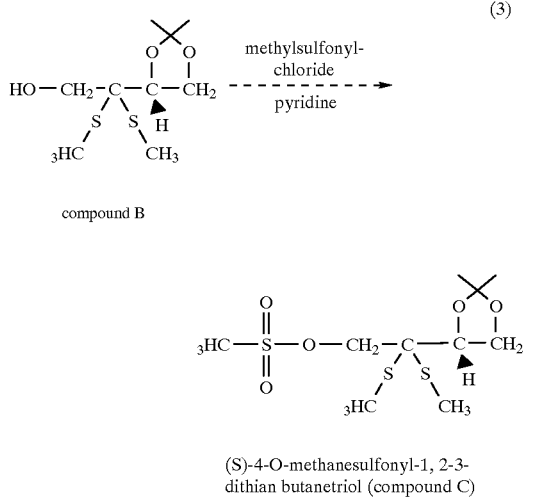

Attachment of a nucleobase to (S)-4-O-methanesulfonyl-1,2-3-dithian butanetriol (compound C)

The following description refers to attachment of adenine, yet as will be appreciated any other native or analog nucleobase may be similarly attached. Thus, a mixture of 8.11 grams (60 mmoles) of adenine and 2.4 grams of a 60% NaH dispersion (60 mmoles) in 200 ml of DMF is stirred for 90 minutes at room temperature. Then, 50 mmoles of compound C are added and the mixture is stirred for further 2.5 hours at 90° C. After evaporation and purification by column chromatography using CHCl$_3$/MeOH (95/5) as an eluent, compound D is obtained.

This process is briefly described by equation 4:

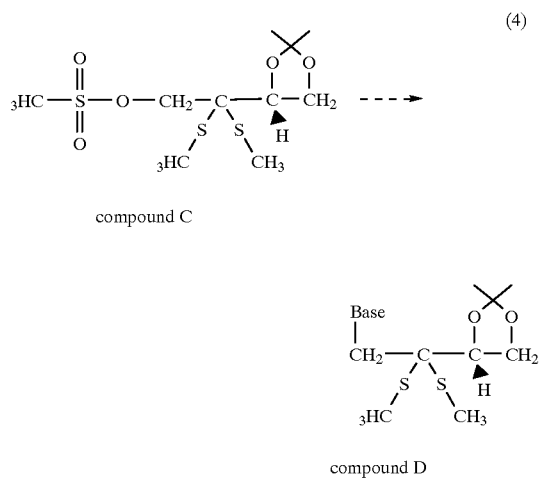

Protection of the amino group of nucleobases as benzoylamido

A portion of 25.3 mmoles of the former stage product (compound D) is co-evaporated with dry pyridine, and dissolved in 225 ml of same. The solution is cooled to 0° C. in an ice-water bath and 4.4 ml (38 mmoles) of benzoylchloride are added. After 15 hours at room temperature, additional amount of 1.47 ml (12.6 mmoles) of benzoylchliride are added, at 0° C. The reaction mixture is stirred at room temperature until TLC-analysis shows complete disappearance of the starting material (typically within two hours). After cooling in ice bath, 75 ml of water and 52 ml of concentrated ammonia are added. The mixture is allowed to warm up gradually to room temperature. After TLC analysis shows almost complete conversion of the dibenzoyl of the monobenzoyl derivative, the mixture is evaporated and purified by extraction with ethanolactetate/H$_2$O (1/1), followed by column chromatography using CHCl$_3$/MeOH (98/2) as the eluent, compound E is obtained.

This process is briefly described by equation 5:

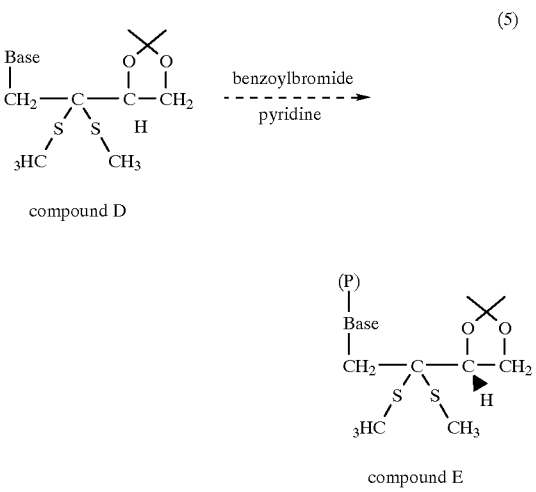

Hydrolysis of the acetonide of compound E

Compound E obtained in the former stage is dissolved in 200 ml of 80% aqueous acetic acid and kept at room temperature for 21 hours followed by 4 hours at 50° C. Evaporation followed by co-evaporation with toluene and crystallization from methanol/ethylacetate (1:9) affords 63% yield of compound F.

This process is briefly described by equation 6:

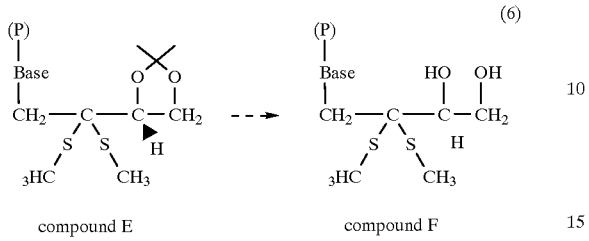

compound E          compound F         (6)

Protection of the hydroxyl of compound F with dimethoxytrityl group

A mixture of 11 mmoles of compound F is co-evaporated with dry pyridine and is thereafter dissolved in 100 ml of same. The mixture obtained is cooled in ice-water bath, and 13.2 mmoles of dimethoxytrityl chloride (Aldrich) dissolved in 75 ml of dry pyridine is added dropwise. The mixture is kept at room temperature for 17 hours, afterwhich the mixture is evaporated to dryness and extracted with ethylacetate/water (1:1), washed once with 100 ml saturated NaHCO$_3$ solution, twice with water and twice with brine solution. The organic layer is dried over anhydrous sodium sulfate, evaporated and purified by column chromatography using CH$_2$Cl$_2$/MeOH (95/5) to yield compound G.

This process is briefly described by equation 7:

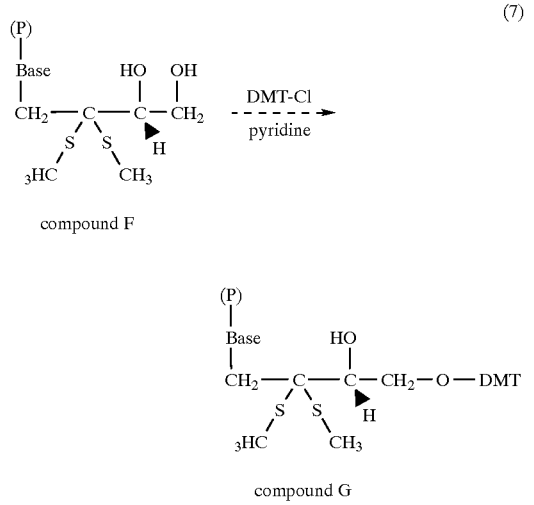

compound F compound G          (7)

Reaction of compound G with ethylene dibromide

A mixture of 10 mmoles of compound G obtained in the former stage, and 10 mmoles of NaH in 50 ml dry DMF are stirred at –20° C. under Argon atmosphere. To this mixture, 50 mmoles of ethylene dibromide (Aldrich) dissolved in 50 ml DMF are added dropwise. The mixture is then allowed to warm to room temperature and is stirred for one hour. Water is added dropwise and the product is extracted with ethylacetate, washed with brine, dried over sodium sulfate and evaporated to dryness. The oily product is chromatographed on a silica gel using CH$_2$Cl$_2$/MeOH (98/2) as the eluent to yield compound H, which is presently a preferred building block for ENA, following general formula V.

This process is briefly described by equation 8:

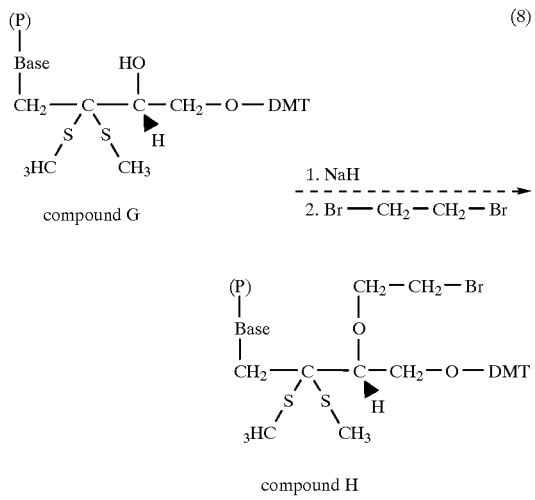

compound G compound H          (8)

It will be appreciated that using the above described stages 1–8, one can produce monomers differing in the nucleobase attached thereto, which monomers, as is exemplified in the following Examples, can be used to synthesize an ENA compound of a desired preselected sequence.

EXAMPLE 2

Preparation of the Polymeric Support for ENA Synthesis

Preparation of a hydroxy polymer

The preferred polymeric support for solid phase ENA synthesis according to the present invention is a Merrifield's peptide resin, 2% cross-linked (chloromethylated styrene/divinylbenzene copolymer, Aldrich). The chloride groups covalently attached to the polymer via—CH$_2$—groups are replaced by hydroxyl groups, by mixing 10 grams of the polymer with large excess (50 ml) of acetic acid/triethylamine (1/1) and absolute ethanol (100 ml), and heating the mixture at reflux temperature for 48 hours. The polymer is washed with ethanol under vacuum, and resuspended along with 5 grams of KOH in 100 ml methanol for 3 hours, at room temperature. The resulted hydroxy polymer is washed first with water then by methanol and is dried by washing with ether.

This process is briefly described by equations 9–10:

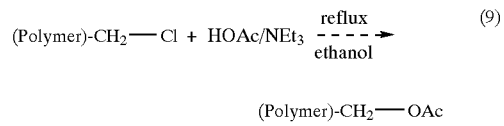

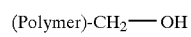

The hydroxy polymer is allowed to react with 1,4-dibromo-2,3-isopropylidene butanediol by the following reactions.

Preparation of 1,4-dibromo-2,3-isopropylidene-2,3-butanediol 1,4-dibromo-2,3-butanediol (24.8 grams, 100 mmoles, Aldrich) is dissolved in 200 ml dry acetone, containing a catalytic amount (1.9 grams, 10 mmoles) of p-toluenesulfonic acid. The mixture is stirred at room temperature for 3 hours. After addition of 1.6 grams sodium acetate (20 mmoles), the mixture is filtered and the residue is chromatographed on silica gel using $CH_2Cl_2$/hexane (9/1) to afford 27 grams (93%) as an oil.

This process is briefly described by equation 11:

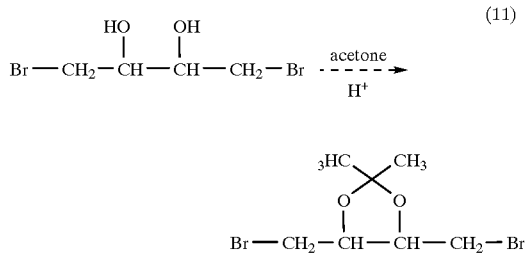

Attachment of the dibromide to the hydroxy-polymer

To five grams of the hydroxy-polymer obtained according to equation 10, two grams of sodium hydride (60% dispersion in mineral oil) are added in a mixture containing 50 ml dried DMF. The suspension is refluxed for 12 hours, followed by addition of five grams of 1,4-dibromo-2,3-isopropylidene-butanediol (a dibromide) in dry DMF. The mixture is agitated at room temperature for 16 hours. The resulting polymer is washed first with dioxane, then by methanol and is dried by washing with ether.

This process is briefly described by equation 12:

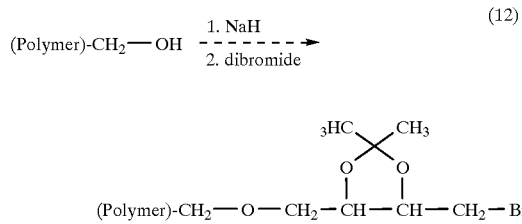

Converting the polymer-bromide to alcohol

Five grams of the polymer-bromide formed in the last step, are allowed to react with a mixture of 50 ml acetic acid/triethylamine (1/1) and 100 ml absolute ethanol. The suspension is refluxed for 48 hours, the polymer is washed with methanol and dried with ether. The dried polymer is suspended along with five grams of KOH in 100 ml methanol at room temperature for 3 hours.

This process is briefly described by equation 13:

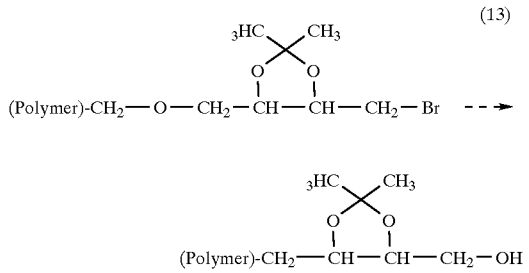

The resulting hydroxy group of the polymer thus obtained is ready to be condensed with the bromide of compound H, which is the preferred building block V of the present invention.

EXAMPLE 3

ENA Synthesis (The Cycle)

The cycle of ENA synthesis includes three steps: condensation, capping and deprotection.

Condensation

To a suspension of 1 gram of the polymeric support in 10 ml dry DMF, 0.5 gram NaH (60% dispersion in mineral oil) in 10 ml dry DMF are added. The suspension is agitated at room temperature for 1 hour followed by addition of 2 grams of a first compound following formula V to which a first base ($B_1$) is attached (e.g., compound H-$B_1$) in dry DMF. The mixture is agitated at room temperature for 2 hours. The suspension is washed with 10 ml methanol and with 10 ml dichloromethane.

This process is briefly described by equation 14:

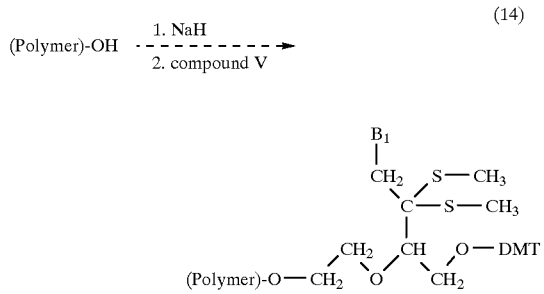

Capping

Acetylation of unreacted polymer hydroxy groups is achieved by adding 10 ml of acetic anhydrid/lutidine/tetrahydrofuran (1/1/8) to the polymeric support resulted from the previous step. The suspension is agitated for five minutes. Then, the solvent is sucked by vacuum, washed twice with 10 ml methanol and twice with 10 ml dichloromethane.

Deprotection of the dimethoxytrityl group (DMT)

The dried polymer resulting from the previous step, is treated with 5 ml of 2% of trichloroacetic acid in dichloromethane for one minute, the orange color is monitored spectrometrically, the polymer is washed with methanol and with dry ether.

The dried polymer is then condensed with a second compound following formula V to which a second base ($B_2$) is attached (e.g., compound H-$B_2$) in dry DMF in a manner as described above under condensation. Such cycles are repeated as much as needed to form appropriate antisense sequence, wherein in each tri-stages cycle one additional monomer is sequentially added to the growing chain.

When cycling is completed, few deprotection steps are performed as follows:

Deprotection of amino groups containing bases

The polymeric support to which the antisense sequence is attached, is treated with concentrated ammonium hydroxide for 16 hours at 55° C. The polymeric support is washed with water, methanol and with ether.

Deprotection of the dithian (S-C-S) group

The polymeric support is further treated with a solution of two grams of silver perchlorate dissolved in 20 ml of a mixture of water/benzene (1/1) for 4 hours at room temperature. The resulted polymer is washed with water, then with methanol and ether.

Deprotection of the isopropylene group from the polymeric support

The polymeric support resulted from the previous step is treated with a solution of 80% aqueous acetic acid and agitated at room temperature for 21 hours and for 4 hours at 50° C. The polymer is washed with water, methanol and ether.

At this stage the ether nucleic acid is ready and id detached from the supporting polymer as follows.

Deprotection of ENA from the polymeric support

The polymeric support is further treated with a solution of one gram sodium periodate in 10 ml water for 3 hours. In order to reduce the aldehyde group thus formed, one gram of solid sodiumborohydride is added and the solution is stirred for one hour at room temperature. The solution is collected and purified by dialysis against water for 16 hours at 4° C., followed by HPLC purification.

Should PEG exoconjugates be attached to the ENA compound formed, after treating the polymeric support-ENA with sodium periodate as described above, two grams of amino-polyethyleneglycol (PEG-NH$_2$, see Example 3 below) are added, followed by addition of 250 mgrams of cyanoborohydride. The mixture is stirred for 5 hours at room temperature, and the PEG-ENA purified as described above.

EXAMPLE 4

Preparation of PEG-NH$_2$

Poly(ethylene glycol) (PEG) is a water soluble polymer that when covalently linked to other substrates such as proteins, alters their properties in ways that extent their potential uses. The improved pharmacological performance of PEG-protein conjugates when compared with their unmodified protein counterparts prompted the development of this type of PEG conjugates as therapeutic agents. For example, enzyme deficiencies, e.g., adenine deaminase (ADA) deficiency, for which therapy with native enzymes was found inefficient due to rapid clearance and/or immunological reactions can now be treated with equivalent PEG-enzymes, e.g., PEG—ADA. This novel observation may open new horizons to the application of PEGylation technology.

Covalent attachment of PEG to ENA requires activation of the hydroxyl terminal group of the PEG polymer with a suitable leaving group that can be displaced by nucleophilic attack with nucleophiles.

Activation of PEG could be achieved for example by converting its terminal hydroxyl group into a leaving amino group to obtain PEG—NH$_2$.

PEG can be converted into PEG—NH$_2$ by the following way (equations 15–17):

$$\text{PEG—O—CH}_2\text{—CH}_2\text{—OH} + \text{Tosyl-chloride} \rightarrow \text{PEG—O—CH}_2\text{—CH}_2\text{—O—Tosyl} \quad (15)$$

$$\text{PEG—O—CH}_2\text{—CH}_2\text{—O—Tosyl} + \text{NaN}_3 \rightarrow \text{PEG—O—CH}_2\text{—N}_3 \quad (16)$$

$$\text{PEG—CH}_2\text{—CH}_2\text{—N}_3 + \text{H}_2/\text{Pd(C)} \rightarrow \text{PEG—O—CH}_2\text{—CH}_2\text{NH}_2 \quad (17)$$

The PEG—NH$_2$ derivative can be condensed with carboxylic activated groups to form an amid linkage connecting an ENA molecule according to the invention with PEG, according to equation 18:

$$\text{PEG—O—CH}_2\text{—CH}_2\text{—NH}_2 + \underset{\text{succinimidyl}}{\text{N—O—CO—ENA}} \rightarrow \quad (18)$$

$$\text{PEG—O—CH}_2\text{—CH}_2\text{—NH—CO—ENA}$$

The PEG—NH$_2$ derivative can alternatively be condensed with an aldehyde to form a Shiff base, which condensation is followed by reduction to an amino linkage connecting an ENA molecule according to the invention with PEG, according to equation 19:

$$\text{PEG—O—CH}_2\text{—CH}_2\text{—NH}_2 + \text{O}=\text{C—ENA} \xrightarrow{NaBH_4} \text{PEG—O—CH}_2\text{—CH}_2\text{—NH—CH}_2\text{—ENA} \quad (19)$$

While the invention has been described with respect to a limited number of embodiments, it will be appreciated that many variations, modifications and other applications of the invention may be made.

What is claimed is:

1. A compound comprising a polyether backbone having a plurality of chiral carbon atoms, said polyether backbone bearing a plurality of ligands being individually bound to said chiral carbon atoms, said ligands including a moiety selected from the group consisting of a naturally occurring nucleobase and a nucleobase binding group.

2. The compound of claim 1, wherein said chiral carbon atoms are separated from one another in said backbone by from four to six intervening atoms.

3. A compound having the formula:

$$[K] \underset{\substack{| \\ C \\ | \\ X1}}{\overset{B1}{|}} \underset{C}{\overset{O}{\diagdown}} \underset{O}{\overset{C1}{\diagdown}} \underset{C}{\overset{C}{\diagdown}} \underset{O}{\overset{O}{\diagdown}} \underset{\substack{| \\ C \\ | \\ X2}}{\overset{B2}{|}} \underset{C}{\overset{C2}{\diagdown}} \underset{C}{\overset{C}{\diagdown}} \cdots \underset{\substack{| \\ C \\ | \\ Xn-1}}{\overset{Bn-1}{|}} \underset{O}{\overset{Cn-1}{\diagdown}} \underset{C}{\overset{C}{\diagdown}} \underset{\substack{| \\ C \\ | \\ Xn}}{\overset{Bn}{|}} \underset{O}{\overset{Cn}{\diagdown}} \underset{C}{\overset{C}{\diagdown}} [I]$$

wherein:
n is an integer greater than one;
each of B1, B2, Bn-1 and Bn is a chemical functionality group independently selected from the group consisting of a naturally occurring nucleobase and a nucleobase binding group;
each of X1, X2, Xn-1 and Xn is independently selected from the group consisting of a CH$_2$ group and a C=O group;

C1, C2, Cn−1 and Cn are chiral carbon atoms; and

[K] and [I] are a first and a second exoconjugates.

4. The compound of claim 3, wherein m percents of said chiral carbons are in an S configuration, wherein m is selected from the group consisting of 90–95%, 96–98%, 99% and greater than 99%.

5. The compound of claim 3, wherein [K] and [I] are each a polyethylene glycol moiety.

6. The compound of claim 3, having the formula:

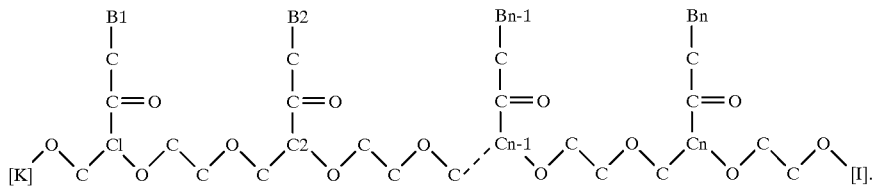

7. A compound having a formula:

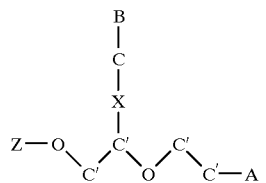

wherein:
B is a chemical functionality group selected from the group consisting of a naturally occurring nucleobase and a nucleobase binding group;
X is selected from the group consisting of a $CH_2$ group and a C=O group;
C' are chiral carbon atoms;
C is a carbon atom;
Z is a first protecting group; and
A is a leaving group.

8. The compound of claim 7, wherein should said nucleobase include an amino group, said amino group is protected by a second protecting group.

9. The compound of claim 7, wherein said Z protecting group is selected from the group consisting of a dimethoxytrityl group, a trityl group, a monomethoxytrityl group and a silyl group.

10. The compound of claim 7, wherein said A leaving group is selected from the group consisting of a halide group, a sulfonate group, an ammonium derivative, and a radical moiety that could be replaced by SN1 or SN2 mechanisms.

11. The compound of claim 8, wherein said second protecting group is selected from the group consisting of a benzamido group, an isobutyramido group, a t-butoxycarbonyl group, a fluorenylmethyloxycarbonyl group and an acid labile group which is not cleaved by reagents that cleave said Z protecting group.

12. The compound of claim 7, having the formula:

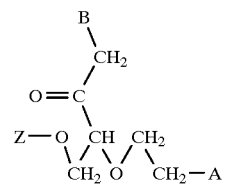

13. A compound having the formula:

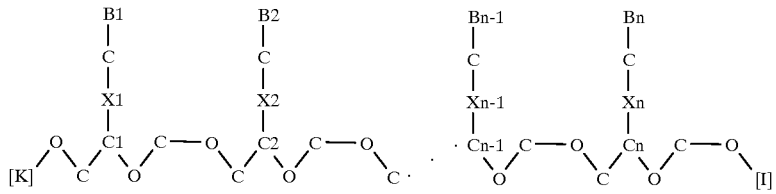

wherein:
n is an integer greater than one;
each of B1, B2, Bn−1 and Bn is a chemical functionality group independently selected from the group consisting of a naturally occurring nucleobase and a nucleobase binding group; p1 each of X1, X2, Xn−1 and Xn is independently selected from the group consisting of a $CH_2$ group and a C=O group;
C1, C2, C−1 and Cn are chiral carbon atoms; and
[K] and [I] are a first and a second exoconjugates.

14. A pharmaceutical composition comprising, as an active ingredient, a compound according to claim 1, and at least one pharmaceutically effective carrier, binder, thickener, dilutent, buffer, preservative or surface active agent.

15. A process for preparing a compound according to claim 1, comprising the steps of:
   (a) obtaining monomers, each of said monomers having an ether moiety, said ether moiety including at least one etheric bond, said ether moiety further including at least one chiral carbon atom to which a functionality group is linked, said functionality group being selected from the group consisting of a naturally occurring nucleobase and a nucleobase binding group;
   (b) attaching a first monomer of said monomers to a solid support; and
   (b) sequentially condensing monomers in a predetermined sequence to said first monomer for obtaining a polymer of condensed monomers.

16. A process for sequence specific hybridization comprising the step of contacting a double stranded polynucleotide with a compound according to claim 1, so that said compound binds in a sequence specific manner to one strand of said polynucleotide, thereby displacing the other strand.

17. A process for sequence specific hybridization comprising the step of contacting a single-stranded polynucleotide with a compound according to claim 1, so that said compound binds in a sequence specific manner to said polynucleotide.

* * * * *